United States Patent [19]

Chen

[11] 4,100,215

[45] Jul. 11, 1978

[54] SELECTIVE PRODUCTION OF PARA-XYLENE

[75] Inventor: Nai Y. Chen, Titusville, N.J.

[73] Assignee: Mobil Oil Corporation, New York, N.Y.

[21] Appl. No.: 727,084

[22] Filed: Sep. 27, 1976

Related U.S. Application Data

[63] Continuation-in-part of Ser. No. 509,188, Sep. 25, 1974, Pat. No. 4,002,697, which is a continuation-in-part of Ser. No. 421,459, Dec. 3, 1973, abandoned.

[51] Int. Cl.² ............................................. C07C 3/52
[52] U.S. Cl. ............................................. 260/671 M
[58] Field of Search ................................... 260/671 M

[56] References Cited

U.S. PATENT DOCUMENTS

| | | | |
|---|---|---|---|
| 3,702,886 | 11/1972 | Argauer et al. | 423/328 |
| 3,751,506 | 8/1973 | Burress | 260/671 M |
| 3,965,207 | 6/1976 | Weinstein | 260/671 M |

*Primary Examiner*—C. Davis
*Attorney, Agent, or Firm*—Charles A. Huggett; Raymond W. Barclay

[57] ABSTRACT

Process for the selective production of paraxylene by methylaton of toluene in the presence of a catalyst comprising a crystalline aluminosilicate zeolite characterized by (1) a silica to alumina ratio of at least about 12, (2) a constraint index within the approximate range of 1 to 12 and (3) a crystal size greater than 1 micron.

10 Claims, No Drawings

SELECTIVE PRODUCTION OF PARA-XYLENE

CROSS REFERENCE TO RELATED APPLICATIONS

This application is a continuation-in-part of copending application Ser. No. 509,188 filed Sept. 25, 1974, now U.S. Pat No. 4,002,697 issued January 11, 1973 which in turn is a continuation-in-part of Ser. No. 421,459 filed Dec. 3, 1973, now abandoned.

BACKGROUND OF THE INVENTION

1. Field of the Invention.

This invention relates to a process for the selective production of para-xylene by catalytic methylation of toluene in the presence of a particular crystalline aluminosilicate catalyst.

2. Description of the Prior Art.

Alkylation of aromatic hydrocarbons utilizing crystalline aluminosilicate catalysts has heretofore been described. U.S. Pat. No. 2,904,607 to Mattox refers to alkylation of aromatic hydrocarbons with an olefin in the presence of a crystalline metallic aluminosilicate having uniform pore openings of about 6 to 15 Angstrom units. U.S. Pat. No. 3,251,897 to Wise describes alkylation of aromatic hydrocarbons in the presence of X- or Y-type crystalline aluminosilicate zeolites, specifically such type zeolites wherein the cation is rare earth and/or hydrogen. U.S. Pat. No. 3,751,504 to Keown et al. and U.S. Pat. No. 3,751,506 to Burress describe vapor phase alkylation of aromatic hydrocarbons with olefins, e.g. benzene with ethylene, in the presence of a ZSM-5 type zeolite catalyst.

Crystalline aluminosilicate zeolites, modified by reaction with an organic substituted silane, have been described in U.S. Pat. No. 3,682,996 to Kerr and in U.S. Pat. No. 3,698,157 to Allen et al. The former of these patents describes, as novel compositions of matter, crystalline aluminosilicate esters made by reacting a crystalline aluminosilicate having and available hydrogen atom with an organic silane having a SiH group. The resulting compositions were disclosed as being catalysts useful for hydrocarbon processes, particularly hydrocracking. In the latter of the above patents, the use of ZSM-5 type crystalline aluminosilicate zeolites modified by treatment with an organic-radical substituted silane are described, together with the use of such modified zeolites in chromatographic separation of the compounds contained in a $C_8$ aromatic feed stock.

While the above-noted prior art is considered of interest in connection with the subject matter of the present invention, the methylation process described herein utilizing the specified catalyst of controlled crystal size crystalline aluminosilicate having a silica to alumina ratio of at least about 12 and a constraint index within the approximate range of 1 to 12 to achieve selective production of para-xylene has not, insofar as is known, been heretofore disclosed.

Of the xylene isomers, i.e. ortho-, meta- and paraxylene, the latter is of particular value being useful in the manufacture of terephthalic acid which is an intermediate in the manufacture of synthetic fibers such as "Dacron". Mixtures of xylene isomers either alone or in further admixture with ethylbenzene, generally containing a concentration of about 24 weight percent para-xylene in the equilibrium mixture, have been previously separated by expensive superfraction and multistage refrigeration steps. Such process, as will be realized, has involved high operation costs and has a limited yield.

SUMMARY OF THE INVENTION

In accordance with the present invention, there has been discovered a process for selectively producing paraxylene in preference to meta- or ortho-xylene by reaction of toluene with a methylating agent in the presence of a catalyst comprising large crystals, i.e., of a size greater than 1 micron and preferably greater than 3 microns, of a crystalline aluminosilicate catalyst having a silica to alumina ratio of at least about 12 and a constraint index, hereinafter defined within the approximate range of 1 to 12.

Compared to a conventional thermodynamic equilibrium xylene mixture in which para:meta:ortho ratio is approximately 1:2:1, the process described herein affords a xylene product having a para xylene concentration substantially greater than that indicated by the thermodynamic equilibrium. The improved para-xylene yield reduces the cost of production and most important the cost separation of para-xylene from its isomers, which is the most expensive step in the current method employed for producing para-xylene.

The present process comprises methylation of toluene, preferably by reaction of the latter with methanol, in the presence of a particular crystalline aluminosilicate zeolite catalyst. The catalyst employed comprises a crystalline aluminosilicate zeolite characterized by: (1) a silica to alumina ratio of at least about 12, (2) a constraint index within the approximate range of 1 to 12 and (3) a crystal size greater than 1 micron. In a preferred embodiment, the specified zeolite of large crystal size has been modified by surface reaction with a material capable of deactivating the external surface thereof.

Such treatment involves contact of the zeolite with suitable compounds of nitrogen or silicon of a size sufficiently large as to be unable to penetrate the zeolite pore structure. A particularly preferred method of surface modification involves reaction of the zeolite with an organic radical substituted silane followed by calcination.

DESCRIPTION OF SPECIFIC EMBODIMENTS

The catalytic composition of this invention comprises a crystalline aluminosilicate zeolite characterized by a silica to alumina ratio of at least about 12, preferably in excess of 30, a constraint index within the approximate range of 1 to 12 and a crystal size greater than 1 micron.

The zeolites herein described are members of a novel class of zeolites exhibiting some unusual properties. These zeolites induce profound transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. This activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalysts useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels Likewise, this ratio excludes silica added in accordance with the present invention, to the crystalline aluminosilicate zeolite after its formation. Although catalysts with a silica to alumina ratio of at least 12 are useful, it is preferred to use catalysts having higher ratios of at least about 30. Such catalysts, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these catalysts ineffective. 12-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary contrained access, a simple determination of the "constraint index" may be made by passing continuously a mixture of an equal weight of normal hexane and 3-methylpentane over a small sample, approximately 1 gram or less, of zeolite at atmospheric pressure according to the following procedure. A sample of the zeolite in the form of pellets or extrudate, is crushed to a particle size about that of coarse sand and mounted in a glass tube. Prior to testing, the zeolite is treated with a stream of air at 1000° F. for at least 15 minutes. The zeolite it then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on a stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical catalysts are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.5 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° to 950° F., with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° to 950° F., the constraint index will have a value for any given zeolite of interest herein within the approximate range of 1 to 12.

The class of zeolites defined herein is exemplified by ZSM-5, ZSM-11, ZSM-12, ZSM-21, ZSM-35, ZSM-38 and other similar materials. U.S. Pat. No. 3,702,886 describing and claiming ZSM-5 is incorporated herein by reference.

ZMS-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

Preparation of synthetic zeolite ZSM-21 is typically accomplished as follows: A first solution comprising 3.3 g. sodium aluminate (41.8% Al₂O₃, 31.6% Na₂O and 24.9% H₂O), 87.0 g. and 0.34 g, NaOH (50% solution with water) was prepared. The organic material pyrrolidine was added to the first solution in 18.2 g. quantity to form a second solution. Thereupon, 82.4 g. colloidal silica (29.5% SiO₂ and 70.5% H₂O) was added to the second solution and mixed until a homogeneous gel was formed. This gel was composed of the following components in mole ratios:

| | |
|---|---|
| $\dfrac{R^+}{R^+ + M^+}$ | 0.87, wherein M is sodium and R is the pyrrolidine ion. |
| $\dfrac{OH^-}{SiO_2}$ | 0.094 (Not including any contribution of OH⁻ from pyrrolidine) |
| $\dfrac{H_2O}{OH^-}$ | 210 (Not including any contribution of OH⁻ from pyrrolidine) |
| $\dfrac{SiO_2}{Al_2O_3}$ | 30.0 |

The mixture was maintained at 276° C. for 17 days, during which time crystallization was complete. The product crystals were filtered out of solution and water washed for approximately 16 hours on a continuous wash line.

X-ray analysis of the crystalline product proved the crystals to have a diffraction pattern as shown in Table I.

TABLE I

| d (A) | I/Io |
|---|---|
| 9.5 ± 0.30 | Very Strong |
| 7.0 ± 0.20 | Medium |
| 6.6 ± 0.10 | Medium |
| 5.8 ± 0.10 | Weak |
| 4.95 ± 0.10 | Weak |
| 3.98 ± 0.07 | Strong |
| 3.80 ± 0.07 | Strong |
| 3.53 ± 0.06 | Very Strong |
| 3.47 ± 0.05 | Very Strong |
| 3.13 ± 0.05 | Weak |
| 2.92 ± 0.05 | Weak |

Chemical analysis of the crystalline product led to the following compositional figures:

| Composition | Wt. % | Mole Ratio on Al₂O₃ Basis |
|---|---|---|
| N | 1.87 | — |
| Na | 0.25 | — |
| Al₂O₃ | 5.15 | 1.0 |
| SiO₂ | 90.7 | 29.9 |
| N₂O | — | 1.54 |
| Na₂O | — | 0.11 |
| H₂O | — | 9.90 |

Physical analysis of the crystalline product calcined 16 hours at 1000° F. showed it to have a surface area of 304 m²/g and adsorption tests produced the following results:

| Adsorption | Wt. % |
|---|---|
| Cyclohexane | 1.0 |
| n-Hexane | 5.4 |
| Water | 9.0 |

In determining the sorptive capacities, a weighed sample of zeolite was heated to 600° C. and held at that temperature until the evolution of basic nitrogeneous gases ceased. The zeolite was then cooled and the sorption test run at 12 mm for water and 20 mm for hydrocarbons.

Zeolite ZSM-21 is described in copending application Ser. No. 560,412, filed Mar. 20, 1975, now U.S. Pat. 4.046,859.

ZSM-38 is more particularly described in U.S. Application Ser. No. 528,060 filed Nov. 29, 1974 and now abandoned. This zeolite can be identified, in terms of mole ratios of oxides and in the anhydrous state, as follows:

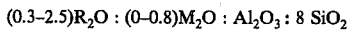
(0.3–2.5)R₂O : (0–0.8)M₂O : Al₂O₃ : 8 SiO₂ wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

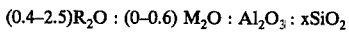
(0.4–2.5)R₂O : (0–0.6) M₂O : Al₂O₃ : xSiO₂ wherein R is an organic nitrogen-containing cation derived from a 2-(hydroxyalkyl) trialkylammonium compound, wherein alkyl is methyl, ethyl or a combination thereof, M is an alkali metal, especially sodium, and x is from greater than 8 to about 50.

The synthetic ZSM-38 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33Å.

TABLE II

| d (A) | I/Io |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-38 is its sorptive capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-38 (after calcination at 600° C.) is less than 10, whereas that ratio for the natural ferrierite is substantially greater than 10, for example, as high as 34 or higher.

Zeolite ZSM-38 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH⁻/SiO$_2$ | 0.05–0.5 | 0.07–0.49 |
| H$_2$O/OH⁻ | 41–500 | 100–250 |
| SiO$_2$/Al$_2$O$_3$ | 8.8–200 | 12–60 | wherein R is an organic nitrogen-containing cation derived from a 2-(hydroxyalkyl) trialkylammonium compound and M is an alkali metal ion, and maintaining the mixture until crystals of the zeolite are formed. (The quantity of OH⁻ is calculated only from the inorganic sources of alkali without any organic base contribution). Thereafter, the crystals are separated from the liquid and recovered. Typical reaction conditiions consist of heating the foregoing reaction mixture to a temperature of from about 90° to about 400° C. for a period of time of from about 6 hours to about 100 days. A more preferred temperature range is from about 150° to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F. for from about 8 to 24 hours.

ZSM-35 is more particularly described in U.S. Application Ser. No. 528,061, filed November 29, 1974, now U.S. Pat. No. 4,016,245. This zeolite can be identified, in terms of mole ratios of oxides and in the anhydrous state, as follows:

(0.3–2.5)R$_2$O : (0–0.8)M$_2$O : Al$_2$O$_3$ : 8 SiO$_2$ wherein R is an organic nitrogen-containing cation derived from ethylenediamine or pyrrolidine and M is an alkali metal cation, and is characterized by a specified X-ray powder diffraction pattern.

In a preferred synthesized form, the zeolite has formula, in terms of mole ratios of oxides and in the anhydrous state, as follows:

(0.4–2.5)R$_2$O : (0.0.6) M$_2$O : Al$_2$O$_3$ : xSiO$_2$ wherein R is an organic nitrogen-containing cation derived from ethylenediamine or pyrrolidine, M is an alkali metal, especially sodium, and x is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33Å. Close examination of some individual samples of ZSM-35 may show a very weak line at 11.3–11.5Å. This very weak line, however, is determined not to be a significant line for ZSM-35.

TABLE III

| d (A) | I/Io |
|---|---|
| 9.6 ± 0.20 | Very Strong – Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 – 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600° C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH⁻/SiO | 0.05–0.5 | 0.07–0.49 |
| H$_2$O/OH⁻ | 41–500 | 100–250 |
| SiO$_2$/Al$_2$O$_3$ | 8.8–200 | 12–60 | wherein R is an organic nitrogen-containing cation derived from pyrrolidine or ethylenediamine and M is an alkali metal ion, and maintaining the mixture until crystals of the zeolite are formed. (The quantity of OH⁻ is calculated only from the inorganic sources of alkali without any organic base contribution). Thereafter, the crystals are separated from the liquid and recovered. Typical reaction conditions consist of heating the foregoing reaction mixture to a temperature of from about 90° to about 400° C. for a period of time of from about 6 hours to about 100 days. A more preferred temperature range is from about 150° to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F., for from about 8 to 24 hours.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-21, ZSM-38 and ZSM-35, with ZSM-5 particularly preferred.

The catalysts of this invention may be in the hydrogen form or they may be base exchanged or impregnated to contain ammonium or a metal cation complement. It is desirable to calcine the catalyst after base exchange. The metal cations that may be present include any of the cations of the metals of Groups I through VIII of the Periodic Table. However, in the case of Group IA metals, the cation content should in no case be so large as to effectively inactivate the catalyst.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erinonite | .35 | 1.51 |
| Gmelinite | .44 | 1.46 |
| Chabazite | .47 | 1.45 |
| A | .5 | 1.3 |
| Y | .48 | 1.27 |

It is a particular feature of the process of this invention that the average crystal size of the selected zeolite employed be greater than 1 micron and preferably greater than 3 microns in diameter and generally in the approximate range of 3 to 10 microns. Without being limited by any theory, the criticality of crystal size would seem to be attributable to the selective production of p-xylene as a result of a balance between the relative rate of diffusion of the xylene isomers and the rate of alkylation. It is postulated that when the latter rate is much faster than the diffusion rate, p-xylene would be the predominant product. Techniques utilized to obtain zeolite crystals within the foregoing ranges involve reaction of sources of alumina, silica and appropriate sodium compounds. For example, for ZSM-5, reaction of a solution of sodium silicate, aluminum sulfate, sodium chloride and sulfuric acid with tri-n-propylamine and n-propyl bromide.

The zeolite of requisite crystal size is converted from its as synthesized alkali metal form to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups I-B to VIII of the Periodic Table including by way of example, nickel, zinc or rare earth metals.

The crystals of zeolite in a form substantially free of alkali metal, i.e. containing less than 1.5 weight percent alkali metal, are then contacted with a surface modifying agent capable of deactivating catalytic sites located on the external surface of the zeolite. Treatment involves contact with a suitable compound of silicon or nitrogen of a size sufficiently large as to be unable to penetrate the zeolite pore structure. Representative of such compounds are: phenyl carbazole, dimethyl dichloro silane, bis-(tri-methylsilyl)-acetamide, trimethyl chlorosilane and hexamethyl disilazane, substituted phenyl carbazole, such as alkyl phenyl carbazole, N-phenyl, acridine, substituted phenyl acridines, such as alkyl phenyl acridine, N-phenyl phenoxazine, 3-[2-pyridyl]-5,6-diphenyl-1,2,4-triazine and 1,4-di-p-toluidino-5-hydroxy anthraquinone. A particular feasible method of surface modification involves reaction of the zeolite with an organic radical substituted silane and subsequent calcination.

Organic substituted silanes useful in preparing the modified zeolites utilized in the present process are those having the general formula:

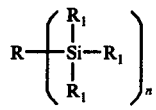

where n is 1 or 2 and R is a reactive group such as hydrogen, alkoxy, halogen, carboxy, amino, acetamide and $R_1$ can be the same group as R or an organic radical which may include alkyl of from 1 up to about 40 carbon atoms, alkyl or aryl carboxylic acid wherein the organic portion of the alkyl group contains about 1 to 30 carbon atoms and the aryl group contains about 6 to 24 carbon atoms, aryl groups of about 6 to 24 carbons, which may be further substituted, alkaryl and aralkyl groups containing about 7 up to about 30 carbon atoms. Preferably, the alkyl group of an alkyl silane is between 1 and 4 carbon atoms in chain length. Mixtures of the above compounds may likewise be used and may, in fact, be preferable from a commerical standpoint.

The selected silane and large crystal size zeolite of low alkali metal content are contacted at an elevated temperature. Generally, the silane and zeolite are contacted on a weight basis of about 2 percent to about 200 percent of zeolite and preferably about 10 to about 100 percent, respectively. The amount of silane should desirably be such as to achieve about 1 to about 5 weight percent of silicon bonded to the outer surface of the zeolite. It is also preferable that a binder for the zeolite be employed, such as for example bentonite. For good contact between the reactants, it is also preferable to employ a reaction medium. Satisfactory reaction media include the ethers, aliphatic hydrocarbons and halo-substituted aliphatic hydrocarbons of 5 to about 8 carbon atoms, aromatic, halo-substituted aromatic hydrocarbons and nitrogen containing compounds such as heterocyclics. A particularly preferred media is pyridine.

An elevated temperature, generally between about 75° and about 200° C., should be employed for the reaction. Usually, the reactants are charged to the medium and heated at the reflux point of the system for about 1 to 10 hours. The mixture is then contacted with a volatile solvent such as chloroform or n-pentane, filtered and dried in an oven at a temperature of about 75° to 125° C. The resulting modified zeolite is considered to have the organic-substituted silane chemically bonded thereto.

Prior to use, the silane-modified zeolite is calcined in an inert atmosphere, e.g. helium or in an oxygencontaining atmosphere, e.g. air. Calcination takes place at a temperature in the approximate range of 300° to 700° C. and preferably between 450° and 550° C.

In practicing the desired methylation process it may be desirable to incorporate the modified zeolite in another material resistant to the temperatures and other conditions employed in the methylation process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the modified zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the modified zeolites employed herein may be composited with a porous matrix material, such as silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of finely divided modified zeolite and inorganic oxide gel matrix may vary widely with the zeolite content ranging from between about 1 to about 99 percent by weight and more usually in the range of about 5 to about 80 percent by weight of the composite. A particularly suitable combination in one containing about 65 weight percent of the zeolite in 35 weight percent of a relatively inactive alumina matrix.

Methylation of toluene in the presence of the above-described catalyst of specified zeolite of crystal size greater than 1 micron is effected by contact of the toluene with a methylating agent, preferably methanol, at a temperature between about 300° and about 700° C. and preferably between about 400° and about 500° C. At the higher temperatures, the zeolites of high silica/alumina ratio are preferred. For example, ZSM-5 of 300 $SiO_2/Al_2O_3$ ratio and upwards is very stable at high temperatures. The reaction generally takes place at atmospheric pressure, but the pressure may be within the approximate range of 1 atmosphere to 1000 psig. A weight hourly space velocity of between about 0.5 and about 10 is employed. The molar ratio of methylating agent to toluene is generally between about 0.5 and about 5. When methanol is employed as the methylating agent a suitable molar ratio of methanol to toluene has been found to be approximately 0.5-2 moles of methanol per mole of toluene. With the use of other methylating agents, such as methylchloride, methylbromide, dimethylether or dimethylsulfide, the molar ratio of methylating agent to toluene may vary within the aforenoted range. Reaction is suitably accomplished utilizing a weight hourly space velocity of between about 0.5 and about 30 and preferably between about 1 and about 10. The reaction product consisting predominantly of para-xylene, together with comparatively smaller amounts of meta-xylene and ortho-xylene may be separated by any suitable means, such as by passing the same through a water condenser and subsequently passing the organic phase through a column in which chromatographic separation of the xylene isomers is accomplished.

The following examples will serve to illustrate the process of this invention without limiting the same:

EXAMPLES 1-5

ZSM-5 crystals of 3 ± 7 micron size were obtained using the following reactants:

Silicate Solution 42.2 lb. Q Brand Sodium Silicate ($Na_2O/SiO_2$ = 3.3)
52.8 lb. Water Acid Solution 612 grams–Aluminum Sulfate 1600 grams–Sulfuric Acid
7190 grams–Sodium Chloride
72.2 lb.–Water Organics 1290 grams Tri-n-propylamine
1110 grams n-Propylbromide The silicate solution and acid solution were nozzle mixed to form a gelatinous precipitate that was charged to a 30 gallon stirred autoclave. When gelation was complete the organics were added and the temperature raised to 315° F. with agitation. The reaction mixture was held at 315° F. with an agitation rate of 121RPM for 17 hours. The product at this time was analyzed by X-ray diffraction and was reported to be ZSM-5. The product was then washed free of soluble salts and dried. Analysis of the product gave the following in terms of mole ratios:

| | |
|---|---|
| $Al_2O_3$ | 1.0 |
| $SiO_2$ | 74.4 |
| $Na_2O$ | 0.31 |
| N | 2.26 |
| C | 21.9 |

The ZSM-5 so prepared was precalcined in air at 370° C. and thereafter ammonium exchanged by contacting twice with 5N $NH_4Cl$ solution at 100° C. (15 ml. per gram zeolite), once for 16 hours, the second time for 4 hours, filtered, washed free of chloride and air dried.

The resulting ammonium form of ZSM-5 was converted to the hydrogen form by calcination in air at 1° C./minute to 538° C. and then held at 538° C. for 10 hours.

Silane treatment of the HZSM-5 so obtained was carried out in reflux pyridine with dimethyl dichlorosilane (8 grams of zeolite, 50 cc of pyridine, 10 cc of dimethyl dichlorosilane) for 2 hours. The product was then filtered while hot, washed with pyridine (100 cc), chloroform (100 cc) and n-pentane (100 cc), pelleted and screened to 30/50 mesh.

A 0.5 gram sample was loaded into a reactor, heated in flowing helium at 200° C. overnight and the temperature was then raised to 500° C. for 30 minutes before use in the methylation run.

Runs were made at 500° C. by passing a liquid feed containing methanol/toluene (2/1 molar ratio) over the catalyst. The reactor effluent passed through a water condenser and a two-phase liquid product collected. For the organic phase, a 35 foot 10% polyphenyl ether on gas chrom R column was used. The column was held at 95° C. until the appearance of o-xylene peak and the temperature was then raised at 8° C./ min. to 180° C. and held for 30 minutes. A summary of the experimental results for Examples 1–5 is presented in Table II below.

TABLE II

| Example | 1 | 2 | 3 | 4 | 5 |
|---|---|---|---|---|---|
| Sample on Stream Time, hr. | 0.5–0.8 | 1.0–1.5 | 2.0–3.0 | 0.5–1.5 | 3.0–4.0 |
| WHSV | 6.6 | 16.4 | 6.6 | 6.6 | 6.6 |
| Temperature, ° C. | 500 | 500 | 500 | 500 | 500 |
| Methanol/Toluene, mol. | 2 | 2 | 2 | 2 | 2 |
| Composition, | | | | | |
| Organic Phase $C_6^-$ | 2.4 | 2.8 | 5.1 | 3.5 | 6.7 |
| Benzene | 0.5 | 0.1 | 0.1 | 0.1 | 0 |
| Toluene | 61.0 | 70.8 | 63.9 | 61.1 | 73.6 |
| p-Xylene | 23.0 | 19.3 | 15.2 | 23.0 | 8.2 |
| m-Xylene | 6.8 | 2.3 | 5.0 | 5.3 | 3.8 |
| o-Xylene | 2.7 | 2.2 | 5.5 | 2.6 | 4.2 |

TABLE II-continued

| Example | 1 | 2 | 3 | 4 | 5 |
|---|---|---|---|---|---|
| Ethyl benzene | — | — | — | — | — |
| Trimethyl benzenes | 3.6 | 2.5 | 5.2 | 4.4 | 3.6 |
| % Toluene Methylated | 33.5 | 24.2 | 29.2 | 33.0 | 18.8 |
| % Xylene as | | | | | |
| para | 71 | 81 | 59 | 74 | 51 |
| meta | 21 | 10 | 19 | 17 | 23 |
| ortho | 8 | 9 | 22 | 8 | 26 |

From the above results, it will be seen that the equilibrium xylene isomer mixture of 23 percent para, 51 percent meta and 26 percent ortho has been improved to a percentage ratio of 81 percent para, 10 percent meta and 9 percent ortho as a result of toluene methylation conducted in the presence of large crystals of HZSM-5 modified by surface silylation with a large silane compound unable to penetrate the intracrystalline pores and subsequent calcination. It is of further interest to note that as the reaction severity increased, the meta/ortho changed from 1/1 to 2/1 approaching the equilibrium value, while the para isomer remained in high concentration.

EXAMPLES 6–8

ZSM-5 crystals of < 0.1 micron size were obtained using the following reactants:

Solution A 858 grams Sodium Aluminate
58 grams Sodium Hydroxide
50 lb. Water

Solution B 160 lb. Q-Brand Sodium Silicate ($Na_2O/SiO_2 = 3.3$)
200 lb. Water

Solution C 20 lb. Tetrapropylammonium bromide
100 lb. Water

Solution D 16 lb. Sulfuric Acid
50 lb. Water

Solution E 60 lb. Sodium Chloride
72 lb. Water

Solution B was combined with Solution C and the resultant solution combined with Solution A. To this mixture was added 480 grams of zeolite ZSM-5 seed crystals. Then the mixture was mixed with Solution D through a mixing nozzle to form a gelatinous precipitate that was discharged into 150 gallon jacketed kettle. After the gel was charged, solution E was added and the mixture thoroughly blended. The reaction mixture was heated with agitation to 210° F. and held for 6 days. The agitation rate was about 30 RPM. The product after 6 days was analyzed by X-ray diffraction and found to be 100 percent ZSM-5. The product was washed free of soluble salts and dried. Analysis of the product gave the following in terms of mole ratios:

| | |
|---|---|
| $Al_2O_3$ | 1.0 |
| $SiO_2$ | 67.7 |
| $Na_2O$ | 0.81 |
| N | 1.31 |

The ZSM-5 so prepared was precalcined in air at 370° C. and thereafter ammonium exchanged, converted to the hydrogen form and silane treated as described above in Examples 1-5.

Methylation of toluene with methanol using the silylated ZSM-5 was carried out at 300°, 400° and 500° C. in the manner described in the previous examples. A summary of the experimental results for these examples is shown in Table III below:

TABLE III

| Example | 6 | 7 | 8 |
|---|---|---|---|
| Sample on Stream Time, Hr. | 0.5–1.5 | 2.0–3.0 | 3.5–4.5 |
| WHSV | 6.6 | 6.6 | 6.6 |
| Temperture, ° C. | 400 | 300 | 500 |
| Methanol/Toluene, mol. | 2 | 2 | 2 |
| Composition, Organic | | | |
| Phase $C_6^-$ | 8.0 | 6.9 | 4.4 |
| Benzene | 0 | 0 | 0 |
| Toluene | 35.2 | 73.0 | 27.5 |
| p-Xylene | 9.6 | 4.2 | 11.9 |
| m-Xylene | 15.9 | 3.8 | 24.5 |
| o-Xylene | 11.0 | 8.1 | 10.4 |
| Ethyl benzene | — | — | — |
| Trimethyl benzenes | 20.2 | 4.0 | 21.4 |
| % Toluene Methylated | 56.2 | 22.5 | 62.0 |
| % Xylene as | | | |
| para | 26 | 26 | 25 |
| meta | 44 | 24 | 52 |
| ortho | 30 | 50 | 23 |

From the above results, it will be evident that with the use of silylated small crystallites of HZSM-5 in methylation of toluene, the isomer distribution at 500° C. did not appreciably change from that of the equilibrium mixture. It is further evident that the use of small crystals, i.e. < 0.1 micron did not afford the desired selective production of para-xylene achieved with the process of the invention.

EXAMPLES 9-12

These examples serve to illustrate the marked difference observed in methylating toluene utilizing ZSM-5 crystals of 3 × 7 micron size compared with use of ZSM-5 crystals of < 0.1 micron size.

The larger ZSM-5 crystals were prepared, ammonium exchanged and calcined as described in Examples 1-5 to yield HZSM-5. The smaller ZSM-5 crystals were prepared, ammonium exchanged and calcined as described in Examples 6-8 to yield the hydrogen form.

Methylation of toluene with methanol using these ZSM-5 catalysts was carried out in the manner described in the previous examples. A summary of the experimental results for these examples is shown in Table IV below.

TABLE IV

| Example | 9 | 10 | 11 | 12 |
|---|---|---|---|---|
| Crystalline Size | 3 × 7 microns | 3 × 7 microns | < 0.1 microns | < 0.1 microns |
| Temp. ° C | 400 | 500 | 260 | 425 |
| WHSV | 6.6 | 6.6 | 4 | 8 |
| Toluene alkylated, Wt. % | 18.8 | 39.2 | 22.6 | 49.0 |
| % Xylenes as | | | | |
| Para | 48 | 46 | 25 | 24 |
| Meta | 30 | 36 | 26 | 49 |
| Ortho | 22 | 18 | 49 | 27 |
| Trimethyl benzenes/Xylenes | .35 | .10 | 0.78 | 0.50 |

It will be evident from the above results that the use of large zeolite crystals, i.e. 3 × 7 micron size, afforded considerably greater yield of p-xylene than the small crystals, i.e. < 0.1 micron size. Moreover, the ratio of para isomer to ortho isomer increased from 1:2 to 2-2.5:1. This ratio using the larger crystal size zeolite thus exceeded the thermodynamic ratio (1:1) providing strong indication that shape selective alkylation reactions were taking place within the intracrystalline cavities of the zeolite.

EXAMPLES 13-16

ZSM-21 crystals of < 0.3 micron size were obtained using the following reactants:

A. Aluminate Solution
330 g. $NaAlO_2$ (43.1% $Al_2O_3$, 33.1 wt.% $Na_2O$)
3.4 g. 50% NaOH solution
870 g. $H_2O$
B. Silica Solution
824 g. Ludox (30% $SiO_2$)
C. 182 g. Pyrrolidine These solutions were mixed together adding solution C to solution A, mixing, then adding solution B and mixing rapidly for 10 minutes. These solutions were mixed directly in a 2 liter stirred autoclave then heated to and held at 135° C. for 17 days until the crystalline product was obtained. The crystalline product was separated from the crystallizing mixture by filtration and washing.

By x-ray analysis the product was shown to be ZSM-21.

The calcined product by analysis had the following composition:

| | |
|---|---|
| $SiO_2$ | 91.1 wt. % |
| $Al_2O_3$ | 5.33 wt. % |
| Na | 0.19 wt. % |

Sorptive properties were as follows:

| | |
|---|---|
| Cyclohexane | 2.1 wt. % |
| n-hexane | 8.2 wt. % |
| $H_2O$ | 11 wt. % |

The surface area was 349 $m^2/g$.

Methylation of toluene with methanol using the above prepared ZSM-21 was carried out utilizing a mole ratio of methanol/toluene of 0.5 in the manner described in the previous examples. A summary of the experimental results for these examples is shown in Table V below.

TABLE V

| Example | 13 | 14 | 15 | 16 |
|---|---|---|---|---|
| Pressure, psig | 400 | 400 | 400 | 14.7 |
| Sample On-Stream Time, Hr. | 23.2 | 24.8 | 27.5 | 49.7 |
| WHSV | 8 | 8 | 4 | 4 |
| Temperature ° C. | 343 | 400 | 400 | 343 |
| Composition, Organic Phase | | | | |
| $C_6^-$ (including benzene) | 0.2 | 1.3 | 1.7 | 0 |
| Toluene | 75.7 | 66.0 | 67.3 | 84.5 |
| p-xylene | 3.8 | 5.2 | 5.0 | 3.3 |
| m-xylene | 8.8 | 11.3 | 11.2 | 3.6 |
| o-xylene | 3.7 | 4.8 | 4.5 | 5.6 |
| Trimethyl benzenes | 7.6 | 10.9 | 9.6 | 2.8 |
| % Toluene Methylated | 23.9 | 32.2 | 30.3 | 15.3 |
| % Xylene as | | | | |
| para | 23 | 24 | 24 | 27 |
| meta | 54 | 53 | 54 | 29 |
| ortho | 23 | 23 | 22 | 44 |

It is evident, from the above results, that the desired selective production of para-xylene was not achieved with crystals of < 0.3 micron in size. It is further to be noted that at 400 psig, the isomers of xylene were close to the composition at equilibrium; while at atmosphere pressure, the isomer distribution was controlled by the kinetics of the alkylation reaction favoring the ortho isomer.

EXAMPLES 17-18

ZSM-21 crystals of 1-4 micron size were obtained using the following reactants:
A. Silicate Solution
  101.6 g. Q-Brand Silicate (28.8 wt.% $SiO_2$, 8.9 wt.% $Na_2O$)
  6.5 g. 50% NaOH solution
  59.8 g. $H_2O$
B. Acid Alum Solution
  19.4 g. $Al_2(SO_4)_3.18H_2O$
  4.5 g. $H_2SO_4$
  174 g. $H_2O$
C. Ethylenediamine 30.0 g.

These solutions were mixed together adding solution C to solution A then adding solution B and mixing vigorously for 15 minutes. The mixture was charged to a polypropylene jar and sealed. This was held for 62 days at 210° F. in a non-stirred state to allow the product to crystallize.

The solid crystalline product was filtered from the slurry and water washed to remove unreacted soluble components and then dried at 230° F.

X-ray analyses established the material as ZSM-21.

Product analysis on dried sample were as follows:

| | |
|---|---|
| N | 3.09 wt. % |
| Na | 0.07 wt. % |
| $Al_2O_3$ | 10.1 wt. % |
| $SiO_2$ | 85.2 wt. % |
| Solids | 88.4 wt. % |

Sorption properties after calcination 16 hours at 1000° F. were:

| | |
|---|---|
| Cyclohexane | 2.2 wt. % |
| n-Hexane | 5.3 wt. % |
| $H_2O$ | 13.9 wt. % |

The surface area was 347 m²/g.

Methylation of toluene with methanol using the above prepared ZSM-21 was carried out employing a mole ratio of methanol/toluene of 0.5 in the manner described hereinabove. A summary of the experimental results for these examples is shown in Table VI below.

TABLE VI

| Example | 17 | 18 |
|---|---|---|
| Pressure, psig | 400 | 400 |
| Sample On-Stream Time, Hr. | 1.5 | 7.0 |
| WHSV | 8 | 8 |
| Temperature ° C. | 400 | 426 |
| Composition, Organic Phase | | |
| $C_6^-$ (including benzene) | 0 | 0 |
| Toluene | 87.0 | 94.2 |
| p-xylene | 4.3 | 1.7 |
| m-xylene | 2.9 | 1.3 |
| o-xylene | 4.3 | 2.3 |
| Trimethyl benzenes | 1.4 | 0.4 |
| % Toluene Methylated | 12.9 | 5.7 |
| % Xylene as | | |
| para | 38 | 32 |
| meta | 25 | 25 |
| ortho | 37 | 43 |

It will be seen from the above data that by increasing the size of the crystals of ZSM-21 from < 0.3 micron to 1-4 micron, the selectivity for p-xylene increased 33 to 65%. The concentration of p-xylene in each instance exceeded its equilibrium value.

EXAMPLES 19-20

The ammonium form of ZSM-5 crystals of 3 × 7 micron size prepared according to Example 1 is calcined at about 1000° F. for 16 hours. Three grams of the calcined material is exchanged with 35 ml. of a 0.5N 2.9/1 zinc chloride/ammonium chloride solution at 110° F. for four hours. The material is then washed with water and dried in air to yield a catalyst having a zinc concentration of about 0.5 weight percent and a sodium content of about 0.1 weight percent.

Methylation of toluene is carried out with methyl chloride by passing a mole ratio of 1:1 of toluene and gaseous methyl chloride over the catalyst at a pressure of 1 atmosphere and a temperature of 400° to 500° C. A summary of the experimental results is shown in Table VII below.

TABLE VII

| Example | 19 | 20 |
|---|---|---|
| Temperature ° C. | 500 | 400 |
| WHSV | 8 | 8 |
| % Toluene Methylated | 45 | 20 |
| % Xylene as | | |
| para | 48 | 50 |
| meta | 35 | 25 |
| ortho | 17 | 25 |

EXAMPLE 21

Five grams of ZSM-21 having a crystal size of 1-4 micron and prepared as in Example 17 are mixed with 2 grams of N-phenyl acridine. The mixture is loaded in a microreactor and heated to 300° C. in flowing hydrogen for 30 minutes to deactivate the external surface activity. By deactivating the surface activity, the selectivity of p-xylene is improved from 32-38 percent to over 40 percent.

EXAMPLE 22

Three grams of HZSM-5 of 3 × 7 micron size prepared as in Examples 1-5 are treated by immersing in a 2% phenyl carbazole solution in acetone for 30 minutes, filtered and air dried at 100° C. The catalyst is loaded in a microreactor and heated to 300° C. in flowing hydrogen for 30 minutes. Thereafter, a feedstock consisting of a 1:1 molal ratio of tolune:methanol is passed over the catalyst at 1 LHSV and 300° C. Twenty percent of the toluene is alkylated. Among the xylenes produced, 60% is para, 20% is meta and 20% is ortho.

EXAMPLES 23-24

These examples illustrate an alternate method of introducing nitrogren poison to the zeolite catalyst.

In a separate experiment, a catalyst of HZSM-5 of 3 × 7 micron size prepared as in Examples 1-5 is tested under the conditions of Example 22. After 1 hour on-stream, the feedstock of toluene and methanol is switched from a pure mixture to one containing 1000 ppm of dissolved phenyl carbazole and the reaction continued. A summary of the results is shown in Table VIII below.

TABLE VIII

| Example | 23 | 24 |
|---|---|---|
| On-Stream Time | 30 minutes | 1.5 hours |

TABLE VIII-continued

| Example | 23 | 24 |
|---|---|---|
| LHSV | 1 | 1 |
| Temperature °C. | 300 | 300 |
| % Toluene Methylated | 25 | 18 |
| % Xylene as | | |
| para | 48 | 60 |
| meta | 17 | 20 |
| ortho | 35 | 20 |
| Trimethylbenzenes/Xylenes | .35 | .10 |

It is seen from the above results that the selectivity for p-xylene is improved with the addition of the nitrogen poison and that the yield of trimethylbenzene also decreased.

EXAMPLES 25-26

A catalyst of HZSM-11 of 3 × 7 micron size is used for methylating toluene with methanol as described in Examples 9-10 with the following results:

TABLE IX

| Example | 25 | 26 |
|---|---|---|
| Temperature °C. | 400 | 500 |
| WHSV | 6.5 | 6.5 |
| % Toluene Methylated | 19 | 40 |
| % Xylene as | | |
| para | 47 | 45 |
| meta | 32 | 37 |
| ortho | 21 | 18 |

It is to be understood that the foregoing description is merely illustrative of preferred embodiments of the invention of which many variations may be made by those skilled in the art within the scope of the following claims without departing from the spirit thereof.

What is claimed is:

1. In a process for manufacture of xylene by reacting toluene with a methylating agent in the presence of a crystalline aluminosilicate zeolite catalyst, the improvement resulting in a proportion of para-xylene greater than the thermodynamic equilibrium proportion of total xylenes which comprises conducting the reaction at a temperature between about 400° and about 500° C in the presence of a catalyst comprising a crystalline aluminosilicate zeolite, which has not undergone prior surface deactivation by treatment with a compound of nitrogen or silicon, characterized by (1) a silica to alumina ratio of at least about 12, (2) a constraint index within the approximate range of 1 to 12 and (3) a crystal size greater than 1 micron.

2. The process of claim 1 wherein said crystal size is greater than 3 microns.

3. The process of claim 1 wherein said methylating agent is methanol, methylchloride, methylbromide, dimethylether or dimethylsulfide.

4. The process of claim 1 wherein said crystal size is in the approximate range of 3 to 10 microns.

5. The process of claim 1 wherein the step of reacting toluene with a methylating agent is carried out at a pressure of between about 1 atmosphere and about 1000 psig, a weight hourly space velocity of between about 0.5 and about 10 employing a molar ratio of methylating agent to toluene of between about 0.5 and about 5.

6. The process of claim 1 wherein said crystalline aluminosilicate is characterized by a silica/alumina ratio in excess of 30.

7. The process of claim 1 wherein the crystalline aluminosilicate catalyst is ZSM-5.

8. The process of claim 1 wherein the crystalline aluminosilicate is ZSM-11.

9. The process of claim 1 wherein the crystalline aluminosilicate is ZSM21.

10. The process of claim 1 wherein said methylating agent is methanol.

* * * * *

UNITED STATES PATENT AND TRADEMARK OFFICE
CERTIFICATE OF CORRECTION

PATENT NO. : 4,100,215
DATED : July 11, 1978
INVENTOR(S) : Nai Y. Chen

It is certified that error appears in the above-identified patent and that said Letters Patent are hereby corrected as shown below:

In Column 6, line 7, "filed March 20, 1975, now U.S. Patent 4,046,859" should be — filed March 20, 1975 —.

In Column 12, line 60, "ZSM-5 crystals of $3 \pm 7$" should be —ZSM-5 crystals of $3 \times 7$ —.

Signed and Sealed this

Third Day of April 1979

[SEAL]

Attest:

RUTH C. MASON
Attesting Officer

DONALD W. BANNER
Commissioner of Patents and Trademarks